(12) United States Patent
Zhang et al.

(10) Patent No.: US 6,592,553 B2
(45) Date of Patent: Jul. 15, 2003

(54) INTRODUCER ASSEMBLY AND METHOD THEREFOR

(75) Inventors: Yongxing Zhang, Little Canada, MN (US); Martin Tze, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 51 days.

(21) Appl. No.: 09/800,265

(22) Filed: Mar. 6, 2001

(65) Prior Publication Data

US 2002/0138041 A1 Sep. 26, 2002

Related U.S. Application Data

(63) Continuation-in-part of application No. 09/610,444, filed on Jul. 5, 2000.

(51) Int. Cl.$^7$ ............................................. A61M 5/178
(52) U.S. Cl. ............................. 604/164.08; 604/164.1; 604/174; 604/263
(58) Field of Search ............................. 128/658, 772, 128/207.29; 604/110, 164.01–168.01, 171, 198, 179, 263, 158–163, 174

(56) References Cited

U.S. PATENT DOCUMENTS

| | | | | |
|---|---|---|---|---|
| 4,166,469 A | | 9/1979 | Littleford ..................... 128/784 |
| 4,291,694 A | * | 9/1981 | Chai ........................... 604/161 |
| 4,412,832 A | | 11/1983 | Kling et al. ................. 604/164 |
| 4,432,752 A | * | 2/1984 | Marlon ........................ 604/500 |
| 4,619,644 A | * | 10/1986 | Scott ........................... 604/160 |
| 4,795,429 A | * | 1/1989 | Feldstein ............. 128/DIG. 26 |
| 4,895,561 A | * | 1/1990 | Mahurkar .................... 604/174 |
| 4,913,704 A | * | 4/1990 | Kurimoto .................... 604/160 |
| 4,915,701 A | * | 4/1990 | Halkyard .................... 604/198 |
| 4,921,479 A | * | 5/1990 | Grayzel ....................... 604/160 |
| 5,049,136 A | * | 9/1991 | Johnson ...................... 604/198 |
| 5,057,086 A | * | 10/1991 | Dillard, III et al. .......... 604/195 |
| 5,057,088 A | * | 10/1991 | Narayanan et al. ......... 604/198 |
| 5,066,277 A | * | 11/1991 | Carrell et al. ................ 604/110 |
| 5,116,326 A | * | 5/1992 | Schmidt ...................... 604/198 |
| 5,147,327 A | * | 9/1992 | Johnson ...................... 604/198 |
| 5,219,338 A | | 6/1993 | Haworth ..................... 604/198 |
| 5,409,469 A | * | 4/1995 | Schaerf ....................... 604/160 |
| 5,429,612 A | * | 7/1995 | Berthier ...................... 604/110 |
| 5,531,701 A | | 7/1996 | Luther ........................ 604/165 |
| 5,582,165 A | * | 12/1996 | Bryan et al. ............ 128/207.14 |
| 5,647,857 A | * | 7/1997 | Anderson et al. ........... 604/160 |
| 5,662,614 A | * | 9/1997 | Edoga .................... 604/167.01 |
| 5,665,073 A | * | 9/1997 | Bulow et al. ................ 604/263 |
| 5,688,253 A | * | 11/1997 | Paradis .................. 604/164.01 |
| 5,713,867 A | * | 2/1998 | Morris .................... 604/164.05 |
| 5,776,111 A | * | 7/1998 | Tesio .......................... 604/174 |
| 5,797,960 A | | 8/1998 | Stevens et al. .............. 606/213 |
| 5,800,432 A | | 9/1998 | Swanson ...................... 606/49 |
| 5,800,496 A | | 9/1998 | Swoyer et al. .............. 607/122 |
| 5,843,038 A | * | 12/1998 | Bailey ......................... 604/158 |
| 5,951,522 A | * | 9/1999 | Rosato et al. ............... 604/162 |
| 6,079,414 A | | 6/2000 | Roth .......................... 128/898 |
| 6,120,480 A | * | 9/2000 | Zhang et al. ........... 604/164.01 |
| 6,228,052 B1 | * | 5/2001 | Pohndorf ................. 604/96.01 |
| 2002/0029994 A1 | * | 3/2002 | Schon ......................... 206/571 |

* cited by examiner

Primary Examiner—Ira S. Lazarus
Assistant Examiner—Andrea M. Ragonese
(74) Attorney, Agent, or Firm—Schwegman, Lundberg, Woessner & Kluth, P.A.

(57) ABSTRACT

An assembly includes an introducing assembly having an elongate tubular sheath which has an external diameter. The sheath, which extends from a distal end to a proximal end, has a bore including an internal diameter sized to receive a dilator therethrough. The sheath includes a movable suture sleeve thereon. A method includes inserting an introducing assembly into a living body, and sliding a protector over a portion of the instrument and into a costoclavicular space.

23 Claims, 3 Drawing Sheets

INTRODUCER ASSEMBLY AND METHOD THEREFOR

CROSS REFERENCE TO RELATED APPLICATION

This application is a continuation-in-part of U.S. patent application Ser. No. 09/610,444, filed on Jul. 5, 2000, entitled SUTURE SLEEVE SYSTEM, the specification of which is incorporated herein by reference.

TECHNICAL FIELD

The present application generally relates to assemblies including introducers and lead assemblies. Specifically, it relates to an introducer assembly and suture sleeve, and lead and a method therefor.

BACKGROUND

Introducer devices are employed for inserting catheters, guide wires, or other medical devices into patients. A typical procedure provides for insertion of a needle into the vasculature of a patient. After insertion of the needle, a guide wire is inserted through the needle, and the needle is removed. The dilator and sheath assembly is inserted over the guidewire, and the dilator may be removed leaving the sheath protruding from the patient's vein or artery. A diagnostic or therapeutic catheter (e.g., a central venous access catheter) or guide wire or other medical device, is then inserted through the sheath into the patient, for example, within the heart.

In some cases, the medical device is implanted through the subclavian vein which passes between the first rib and a clavicle. As a person's upper arm moves, the space between the first rib and clavicle decreases, which decreases the space for the medical instrument therein. This can result in the medical instrument becoming compressed, and potentially stressed cyclically due to arm movements, possibly resulting in reduced longevity of the medical instrument inserted therein.

Accordingly, what is needed is an introducer assembly which allows for instruments to be more easily affixed within a patient. What is also needed is an introducing assembly which simplifies the implantation process and enhances the longevity of the instrument.

SUMMARY

An introducing assembly is provided which includes an elongate tubular sheath having an external diameter. The sheath has a bore including an internal diameter sized to receive a dilator therethrough. The sheath extends from a distal end to a proximal end, and a protector is slidably disposed over the external diameter of at least a portion of the elongate sheath.

Several options for the introducing assembly are as follows. For instance, in one option, a dilator is disposed through the sheath. In another option, the sheath is separable without disruption to an instrument disposed therethrough, for example, where the sheath includes at least one line of weakness therein.

Further options are as follows. For instance, the protector is flexible. In another option, the protector extends from a first end to a second end, and at least the first end is tapered, and/or the second end is tapered. In yet another option, the protector includes one or more grooves thereon. In yet another option, the protector includes a longitudinal slot therein. Optionally, the protector is defined in part by an outer circumference, and the protector includes a means for reducing the outer circumference of the protector.

In another embodiment, an introducing assembly includes an elongate tubular sheath having an external diameter, and the sheath has a bore including an internal diameter sized to receive a dilator therethrough. The sheath extends from a distal end to a proximal end, and a protector is slidably disposed over the external diameter of at least a portion of the elongate sheath. The protector has a longitudinal slot therein.

Several options for the introducing assembly are as follows. For instance, in one option, the protector extends from a first end to a second, and the slot extends from the first end to the second end. In another option, the protector extends from a first end to a second end, and the first end and/or the second end have beveled edges.

A method is also provided herein. The method includes inserting an introducing assembly into a living body, the introducing assembly including an elongate tubular sheath heaving an external diameter, the sheath having a bore including an internal diameter sized to receive a dilator therethrough. The sheath extends from a distal end to a proximal end, and a protector is slidably received over the external diameter of the sheath. The dilator is removably disposed through the sheath. The method further includes inserting the dilator into a vein or artery of the living body, inserting the sheath into the vein or artery, removing the dilator from the sheath, disposing an instrument through the sheath and into the vein or artery, and sliding the protector over a portion of the instrument.

Several options for the method are as follows. For instance, the method further includes securing the protector to the living body. In another option, the method includes separating and removing the sheath without damage to the instrument. Optionally, the method further includes moving the protector to a position in a costoclavicular space.

In yet another embodiment, a method is provided which includes inserting an introducing assembly into a living body. The introducing assembly includes an elongate tubular sheath having an external diameter, the sheath having a bore including an internal diameter sized to receive a dilator therethrough. The sheath extends from a distal end to a proximal end, and the dilator is removably disposed through the sheath. The method further includes inserting the dilator into a vein or artery of the living body, inserting the sheath into the vein or artery, removing the dilator from the sheath, disposing an instrument through the sheath and into the vein or artery, and sliding a protector over a portion of the instrument and into a costoclavicular space.

Several options for the method are as follows. For instance, the method further includes slidably disposing the protector over the sheath. In another option, the method further includes slidably disposing the protector over the instrument prior to disposing the instrument through the sheath. Optionally, the method further includes securing the protector within the costoclavicular space.

Advantageously, the assembly assists in preventing damage to lead insulation and/or lead conductors, resulting in enhanced lead longevity. Since the lead does not require a suture sleeve to be pre-mounted thereon, the outer diameter can be made smaller and more nimble, further allowing for use of a smaller catheter.

These and other embodiments, aspects, advantages, and features of the present invention will be set forth in part in the description which follows, and in part will become apparent to those skilled in the art by reference to the

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
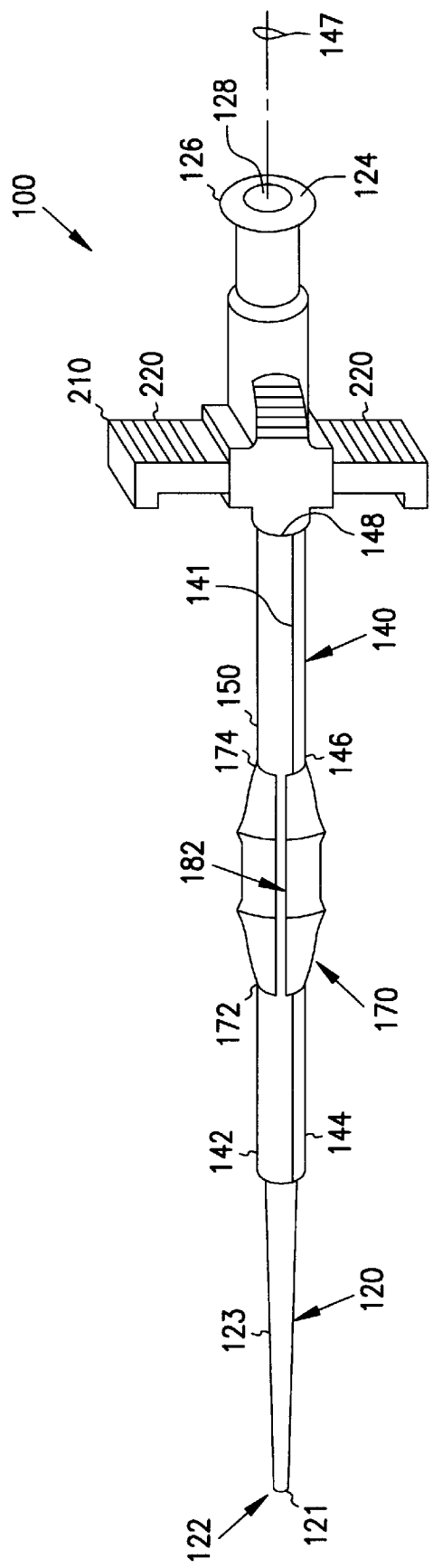
FIG. 1 illustrates a perspective view of an introducing assembly as constructed in accordance with one embodiment.
Figure 2:
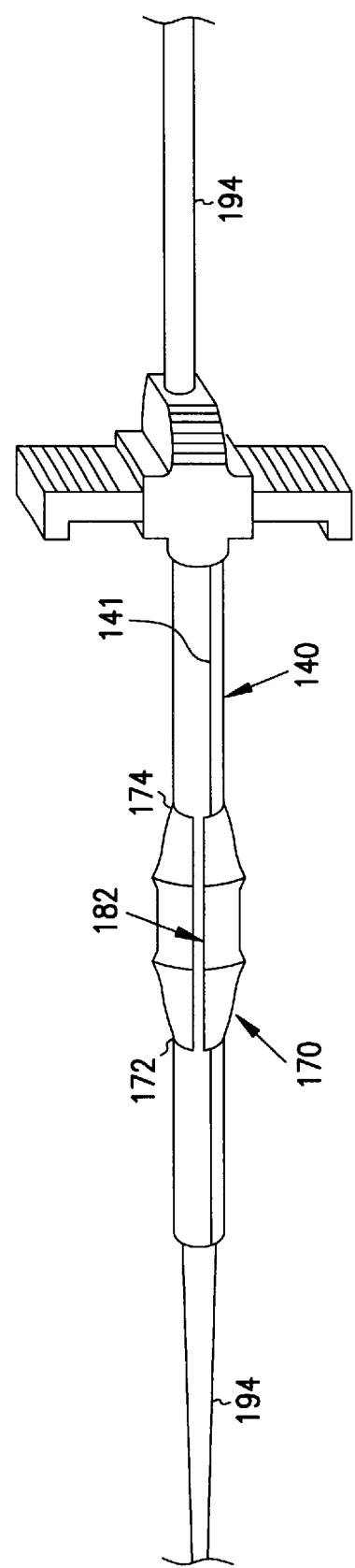
FIG. 2 illustrates a perspective view of an introducing assembly as constructed in accordance with another embodiment.

An introducer assembly 100, as shown in FIG. 1, includes generally a sheath 140 and a dilator 120 received within the sheath 140, and a protector 170 received over the sheath. The dilator 120 allows for the introducer assembly 100 to be introduced into a vein of a patient, for instance, over a guidewire. The dilator 120 extends from a distal end 122 to a proximal end 124, where the distal end 122 is insertable into a patient. The distal end 122 optionally ends in a tapered end 123. At the proximal end 124 is a hub 126 having a bore 128 therethrough. The dilator 120 also includes a passage 121 therethrough, aligned with the bore 128, which allows the dilator 120 to be inserted over a guidewire or a catheter. The dilator 120 is sized to be received by the sheath 140 therein.

The sheath 140 allows for medical instruments to be inserted therethrough and inserted into the patient. The sheath 140, in one option, is removable from a medical instrument inserted therethrough without damage to the medical instrument. The sheath 140 is defined in part by a longitudinal axis 147, and the sheath 140 extends from a distal end 142 to a proximal end 148. The distal end 142 is first inserted into the patient and the proximal end 148 remains outside of the patient. Near the distal end 142 is a tapered portion 144 which provides a transition to a cylindrical portion 146. The sheath 140 also includes a passage therethrough, where the passage is substantially aligned with the longitudinal axis 147 of the sheath 140. The passage allows for the introduction of the dilator 120 therethrough. After the introducer assembly 100 has been inserted into a patient, and the dilator 120 is removed, other medical instruments can be easily inserted into and through the sheath 140, and introduced into the patient.

The sheath 140 optionally includes at least one tab 210 which extends radially outward from the sheath 140. In one embodiment, the sheath 140 includes two tabs 220 which are disposed 180 degrees from each other. Optionally, tab break lines are disposed along the sheath 140, for instance between the two tabs 220.

In another option, the sheath 140 is splittable such that the sheath 140 is separable into two or more components. The sheath 140 is separable or splittable without disruption to or removal of instruments or devices which have been inserted through the sheath 140. The splittable sheath 140 is splittable in a number of manners such as including at least one score line 141. The sheath 140 is externally scored, and optionally two scores 141 are 180 degrees from each other. Alternatively, the sheath 140 is splittable using a slitting device, or a weakening which allows the introducer to be ripped apart, or other techniques which allow the sheath 140 to separate.

Disposed over an outer surface 150 of the sheath 140 is a protector 170. The protector 170 is movably disposed over the outer surface 150, for example, the protector 170 is slidably disposed over the outer surface 150 of the sheath. The protector 170, shown in greater detail in FIGS. 3 and 4, extends from a first end 172 to a second end 174, and is defined in part by a longitudinal axis 180. In one option, the first end 172 is tapered, for example, by including a beveled edge 173. In another option, the second end 174 is tapered, for example, by including a beveled edge 175. The protector 170 is defined by a length 190 which in one option is about 1 inch. In another option, the length 190 is about ½ inch. In yet another option, the length 190 ranges from about ½ inch to an inch. The protector 170 optionally further includes at least one groove 178 which assists in allowing the protector 170 to be sewn in place.

The protector 170 optionally has at least one slot 182 therein (FIG. 1). In one option, the at least one slot 182 is substantially aligned with the longitudinal axis 180. The slot 182 optionally extends from the first end 172 to the second end 174. In another option, the protector 170 includes material which allows for the outer diameter of the protector 170 to be reduced, for example flexible material, or structures which allow for the protector 170 to be flexed. In another option, only a portion of the protector 170 is formed of the flexible material.

The protector 170 is formed of a plastic or elastomeric biocompatible material. Suitable materials for the protector 170 include but are not limited to silicone rubber, polyurethane elastomer, polymers, and co-polymers based on polyolefins, polyesters, polyamides, and fluoropolymers. In one option, the protector 170 is flexible. In another option, the protector 170 is semi-rigid. In yet another option, the protector 170 is radiopaque, for example, by coating or forming the protector 170 with radiopaque material.

Figure 3:
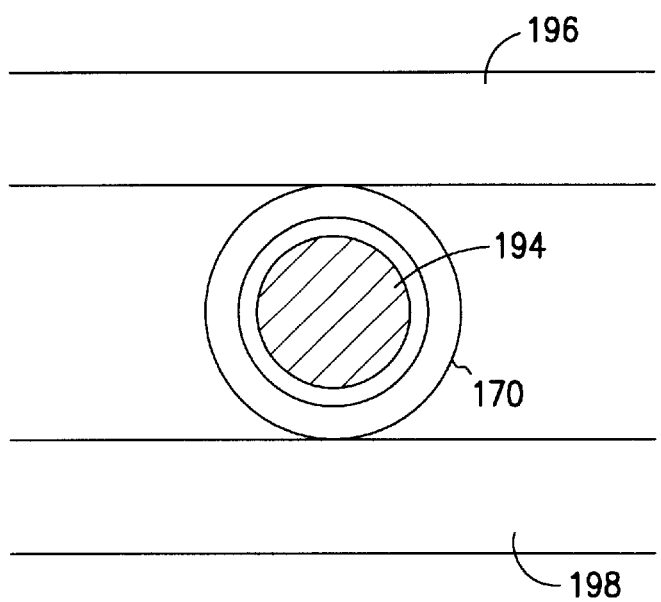
FIG. 3 illustrates a cross sectional view of an introducing assembly as constructed in accordance with one embodiment.
Figure 4:
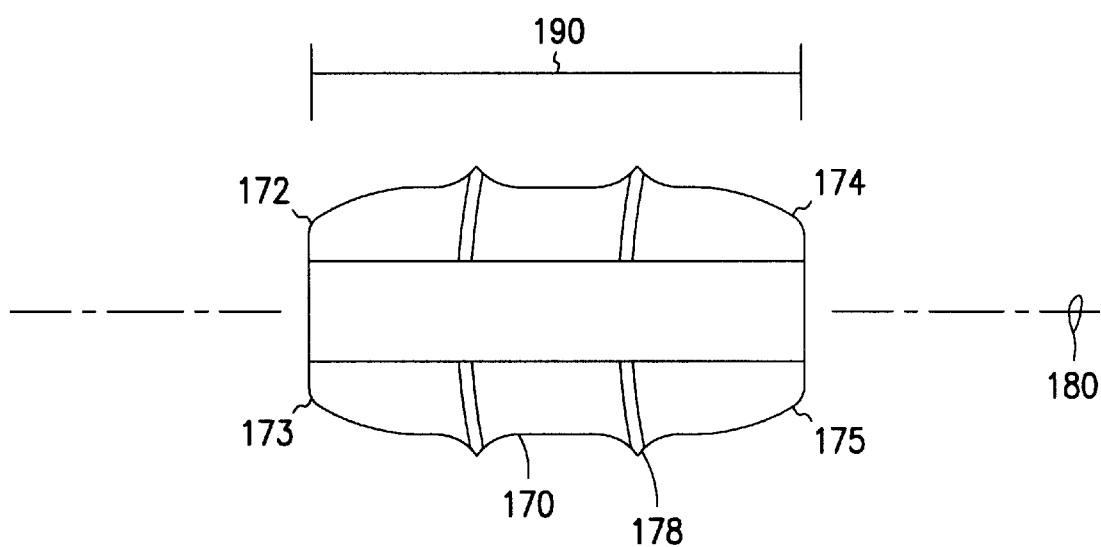
FIG. 4 illustrates a side elevational view of a protector as constructed in accordance with one embodiment.

Several method options are as follows. For example, a hollow needle is inserted into a vein or artery, and a guide wire is passed through the needle and into the vein. The needle is then removed. A protector 170 is mounted on to the sheath 140, and the introducer sheath and dilator assembly 100 is inserted into the vein over the guide wire. The guide wire and the dilator is removed. A lead or other medical instrument 194 is inserted through the sheath into, for example, a subclavian vein and SVC, and into the heart. The protector 170 is moved from the sheath and into the costoclavicular space, for example, between the clavicle 196 and the first rib 198 of a patient (FIG. 3). The sheath is removed from the medical instrument 194, and the protector 170 is mounted on the lead and secured in place.

In another embodiment, the method includes inserting an introducing assembly into a living body, the introducing assembly including an elongate tubular sheath heaving an external diameter, the sheath having a bore including an internal diameter sized to receive a dilator therethrough. The sheath extends from a distal end to a proximal end, and a protector is slidably received over the external diameter of the sheath. The dilator is removably disposed through the sheath. The method further includes inserting the dilator into a vein or artery of the living body, inserting the sheath into the vein or artery, removing the dilator from the sheath, disposing an instrument through the sheath and into the vein or artery, and sliding the protector over a portion of the instrument.

Several options for the method are as follows. For instance, the method further includes securing the protector to the living body. In another option, the method includes separating and removing the sheath without damage to the instrument. Optionally, the method further includes moving the protector to a position in a costoclavicular space, for example by sliding the protector into the space. In another option, sliding the protector over the instrument includes peeling and removing the sheath while pushing the protector over the instrument. In addition or in alternative, the opening to the living body is cut down to find the vein, and the protector is positioned therein.

In yet another embodiment, a method includes inserting an introducing assembly into a living body. The introducing assembly includes an elongate tubular sheath having an external diameter, the sheath having a bore including an internal diameter sized to receive a dilator therethrough. The sheath extends from a distal end to a proximal end, the dilator is removably disposed through the sheath. The method further includes inserting the dilator into a vein or artery of the living body, inserting the sheath into the vein or artery, removing the dilator from the sheath, disposing an instrument through the sheath and into the vein or artery, and sliding a protector over a portion of the instrument and into a costoclavicular space.

Several options for the method are as follows. For instance, the method further includes slidably disposing the protector over the sheath. In another option, the method further includes slidably disposing the protector over the instrument prior to disposing the instrument through the sheath. Optionally, the method further includes securing the protector within the costoclavicular space.

Advantageously, the assembly assists in preventing fracture of lead insulation and/or lead conductors, resulting in enhanced lead longevity. Since the lead does not require a suture sleeve to be pre-mounted thereon, the outer diameter can be made smaller and more nimble, further allowing for use of a smaller catheter.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An introducing assembly comprising:
   an elongate tubular sheath having an external diameter, the sheath having a bore including an internal diameter sized to receive a dilator therethrough;
   the sheath extending from a distal end to a proximal end;
   a protector that includes a bore, the sheath positioned within the bore such that the sheath is slidably disposed over the external diameter of at least a portion of the elongate sheath, and
   wherein the protector includes a longitudinal slot that decreases in size as the protector is compressed.

2. The introducing assembly as recited in claim 1, wherein the dilator is disposed through the sheath.

3. The introducing assembly as recited in claim 1, wherein the sheath is separable without disruption to an instrument disposed therethrough.

4. The introducing assembly as recited in claim 3, wherein the sheath includes at least one line of weakness therein.

5. The introducing assembly as recited in claim 1, wherein the protector is a flexible protector.

6. The introducing assembly as recited in claim 1, wherein the protector extends from a first end to a second end, and at least the first end is tapered.

7. The introducing assembly as recited in claim 6, wherein the second end is tapered.

8. The introducing assembly as recited in claim 1, wherein the protector includes one or more grooves thereon.

9. The introducing assembly as recited in claim 1, wherein the longitudinal slot in the protector decreases in size to reduce the outer circumference of the protector.

10. The introducing assembly as recited in claim 1, wherein the protector has a length of about ½ inch to 1 inch.

11. The introducing assembly as recited in claim 1, wherein the protector has a length of about 1 inch.

12. An introducing assembly comprising:
   an elongate tubular sheath having an external diameter, the sheath having a bore including an internal diameter sized to receive a dilator therethrough;
   the sheath extending from a distal end to a proximal end; and
   a protector that includes a bore, the sheath positioned within the bore such that the sheath is slidably disposed over the external diameter of at least a portion of the elongate sheath, the protector having a longitudinal slot therein that decreases in size to reduce the outer circumference of the protector.

13. The introducing assembly as recited in claim 12, wherein the protector extends from a first end to a second, and the slot extends from the first end to the second end.

14. The introducing assembly as recited in claim 13, wherein the protector extends from a first end to a second end, at least one of the first and second ends having a beveled edge.

15. A method comprising:
   inserting an introducing assembly into a living body, the introducing assembly including an elongate tubular sheath having an external diameter, the sheath having a bore including an internal diameter sized to receive a dilator therethrough;
   the sheath extending from a distal end to a proximal end;
   a protector with a longitudinal slot, the protector including a bore, the sheath positioned within the bore such that the sheath is slidably received over the external diameter of the sheath; and
   the dilator removably disposed through the sheath;
   inserting the sheath and dilator into a vein or artery;
   removing the dilator from the sheath;
   disposing an instrument through the sheath and into the vein or artery; and sliding the protector over a portion of the instrument into the living body such that the protector is compressed by the living body and the longitudinal slot in the protector decreases in size.

16. The method as recited in claim 15, further comprising securing the protector to the living body.

17. The method as recited in claim 15, further comprising separating and removing the sheath without damage to the instrument.

18. The method as recited in claim 15, further comprising moving the protector to a position in a costoclavicular space.

19. The method as recited in claim 15, wherein sliding the protector over the instrument includes peeling and removing the sheath while pushing the protector over the instrument.

20. A method comprising:

inserting an introducing assembly into a living body, the introducing assembly including an elongate tubular sheath heaving an external diameter, the sheath having a bore including an internal diameter sized to receive a dilator therethrough;

the sheath extending from a distal end to a proximal end; and the dilator removably disposed through the sheath;

inserting the dilator into a vein or artery of the living body;

removing the dilator from the sheath;

disposing an instrument through the sheath and into the vein or artery; and sliding a protector that includes a bore over a portion of the instrument and into a costoclavicular space such that the costoclavicular space compresses the protector and decreases the size of a longitudinal slot in the protector.

21. The method as recited in claim 20, further comprising slidably disposing the protector over the sheath.

22. The method as recited in claim 20, further comprising slidably disposing the protector over the instrument prior to disposing the instrument through the sheath.

23. The method as recited in claim 20, further comprising securing the protector within the costoclavicular space.

* * * * *

UNITED STATES PATENT AND TRADEMARK OFFICE
CERTIFICATE OF CORRECTION

PATENT NO.     : 6,592,553 B2
DATED          : July 15, 2003
INVENTOR(S)    : Martin Tze and Yongxing Zhang It is certified that error appears in the above-identified patent and that said Letters Patent is hereby corrected as shown below:

Column 6,
Line 47, delete "claim 13" and insert -- claim 12 --

Column 7,
Line 18, delete "heaving" and insert -- having -- therefor.

Signed and Sealed this

Sixteenth Day of December, 2003

JAMES E. ROGAN
*Director of the United States Patent and Trademark Office*